US009643973B1

(12) United States Patent
Bristow

(10) Patent No.: US 9,643,973 B1
(45) Date of Patent: May 9, 2017

(54) CRYSTALLINE FORM OF DICLOSULAM, A PROCESS FOR ITS PREPARATION AND USE OF THE SAME

(71) Applicant: Rotam Agrochem International Company Limited, Chai Wan (HK)

(72) Inventor: James Timothy Bristow, Chai Wan (HK)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 0 days.

(21) Appl. No.: 14/989,992

(22) Filed: Jan. 7, 2016

(51) Int. Cl.
*C07D 487/04* (2006.01)
*A01N 43/90* (2006.01)
*A01N 25/12* (2006.01)
*A01N 25/14* (2006.01)

(52) U.S. Cl.
CPC .......... *C07D 487/04* (2013.01); *A01N 43/90* (2013.01); *C07B 2200/13* (2013.01)

(58) Field of Classification Search
CPC ....... A01N 47/36; A01N 43/90; C07D 487/04
See application file for complete search history.

(56) References Cited

U.S. PATENT DOCUMENTS 5,163,995 A 11/1992 Van Heertum et al.
6,420,381 B1 * 7/2002 Muraoka .............. C07D 471/04 514/300
2015/0031877 A1 * 1/2015 Hiratsuka .............. A01N 43/84 544/105

OTHER PUBLICATIONS

McClurg, R.B., "X-Ray Powder Diffraction (XRPD) to Describe Crystal Forms," Publication of SSCI an Aptuit Company, Jul. 9, 2008, pp. 1-23.*
Diclosulam Product Safety Assessment, The Dow Chemical Company, Jun. 17, 2012.*
Roberts, R.M. et al. Modern Experimental Organic Chemistry. Holt, Rinehart and Winston, New York, 1979, pp. 49-58.*

* cited by examiner

*Primary Examiner* — John Pak
(74) *Attorney, Agent, or Firm* — Dickinson Wright PLLC

(57) ABSTRACT

A crystalline form of diclosulam of formula (I), the crystal preparation process, the analyses of the crystal through various analytical methods and using the crystal to prepare stable agrochemical formulation. The invention also describes the use of various solvents towards the crystalline form preparation conditions.

(I)

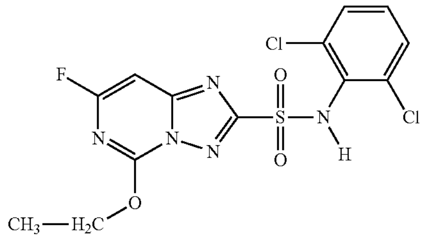

11 Claims, 4 Drawing Sheets

CRYSTALLINE FORM OF DICLOSULAM, A PROCESS FOR ITS PREPARATION AND USE OF THE SAME

BACKGROUND

The present disclosures relates to a crystalline form of (2',6'-dichloro-5-ethoxy-7-fluoro[1,2,4]triazolo[1,5-c]pyrimidine-2-sulfonanilide) (diclosulam), to its preparation processes and to its use in agrochemical preparations.

DESCRIPTION OF RELATED ART

Diclosulam, (2',6'-dichloro-5-ethoxy-7-fluoro[1,2,4]triazolo[1,5-c]pyrimidine-2-sulfonanilide) is a member of the sulfonanilide group of chemicals and used as herbicide. It is having a wide herbicide activity spectrum for controlling weeds such as grasses, broadleaf weeds either for pre or post emergence treatment. But, it has a better activity when applied for the pre-emergence treatment of weeds. The active ingredient is absorbed by the roots, foliage and shoots of the weed species and works by inhibiting the AcetoLactate Synthase (ALS) enzyme which is responsible for the synthesis of proteins required for cell division and plant growth, and hence, the weeds will start discolor and die within few days after the treatment.

Diclosulam has molecular formula of $C_{13}H_{10}Cl_2FN_5O_3S$. Its chemical structure is (I)

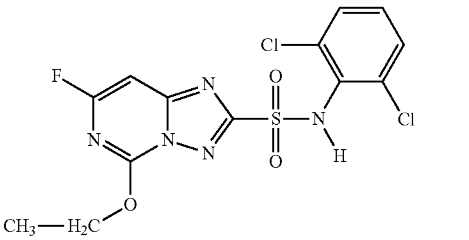

SUMMARY

The commercially available diclosulam, which is usually manufactured by the process described in U.S. Pat. No. 5,163,995, which is incorporated herein by reference for all purposes, is present in an amorphous state. It has been found that diclosulam in amorphous state is highly viscous, which is not suitable for being prepared as compositions or formulations having spray equipment cleanout property. Diclosulam residues stay in the spray equipment after spraying. Adequate cleanout prior to reuse of the spray equipment will typically require a rinsing procedure that is not only time-consuming but also results in wastewater disposal problem. Therefore, there is a need to provide a novel form of diclosulam with improvement with increased solubility and decreased viscosity.

Accordingly, an embodiment of the invention provides a novel crystalline form of diclosulam, termed "crystalline modification I", and a process for its preparation, as well as agrochemical compositions containing it, and methods for using it in agrochemical applications, such as methods for applying to plants, surroundings, and plant parts. The novel crystalline modification I has been advantageously found to have increased solubility, decreased viscosity, and improved spray equipment clean-out properties.

Accordingly, an embodiment of the invention also provides compositions for controlling the growth of undesirable plants, such as weeds, comprising the crystalline modification I of diclosulam on its own, as a mixture with auxiliaries and carriers, and as a mixture with other active compounds. The use of the crystalline modification I of diclosulam in the control of undesired plant growth and a method for the same are also provided by an embodiment of the invention.

BRIEF DESCRIPTION OF DRAWINGS

Various features and aspects of the embodiments of the invention disclosed herein can be more clearly understood by reference to the drawings, which are intended to exemplify and illustrate, but not to limit the scope of the invention, and wherein.

DETAILED DESCRIPTION OF SPECIFIC EMBODIMENTS

Figure 1:
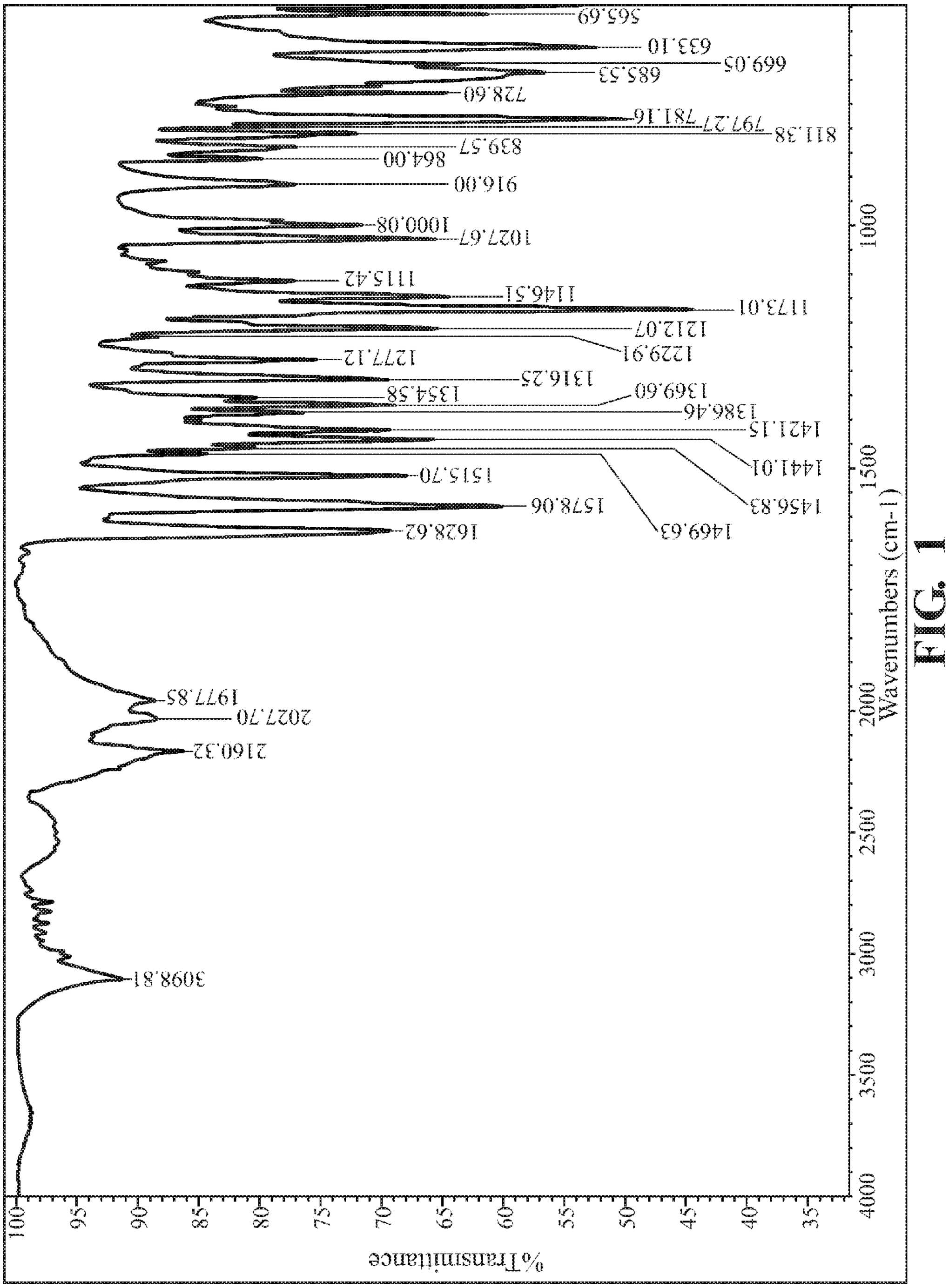
FIG. 1 is an infrared (IR) spectra of an embodiment of crystalline modification I of diclosulam.

The invention can be more clearly understood by reference to the following detailed description of specific embodiments thereof, which is intended to illustrate, but not limited to the scope of the appended claims.

It has been found that the crystalline modification I of diclosulam has a significant increase in its solubility and a significant decrease in its viscosity, which significantly reduces the residue contamination and improves spray equipment clean-out properties. In addition, it is found that the crystalline modification I of diclosulam is easier to comminute or grind compared to amorphous diclosulam prepared in accordance with the disclosure of U.S. Pat. No. 5,163,995. This allows the preparation of commercial formulations such as suspension concentrates (SC), oil-based suspension concentrates (OD), water-dispersible granules (WG) and water-soluble granules (SG). Hence, it is possible to prepare wide range of formulations of diclosulam in crystalline modification I as disclosed hereinafter.

By virtue of its high solubility and low viscosity, the crystalline modification I of diclosulam is highly suitable for preparing compositions for controlling undesirable plants, such as weeds.

According to an embodiment of the invention, a crystalline modification I of diclosulam is provided, exhibiting at least 3 of the following reflexes, in any combination, as 20 values in an X-ray powder diffractogram recorded using Cu-Kα radiation at 25° C.:

$$2\theta=8.09\pm0.2 \quad (1)$$

$$2\theta=8.95\pm0.2 \quad (2)$$

$$2\theta=10.81\pm0.2 \quad (3)$$

$$2\theta=13.25\pm0.2 \quad (4)$$

$$2\theta=16.02\pm0.2 \quad (5)$$

$$2\theta=16.44\pm0.2 \quad (6)$$

2θ=16.68±0.2 (7)

2θ=18.64±0.2 (8)

2θ=18.82±0.2 (9)

2θ=19.63±0.2 (10)

2θ=20.83±0.2 (11)

2θ=23.06±0.2 (12)

2θ=24.51±0.2 (13)

2θ=25.72±0.2 (14)

2θ=26.15±0.2 (15)

2θ=26.70±0.2 (16)

2θ=26.92±0.2 (17)

2θ=27.72±0.2 (18)

Figure 2:
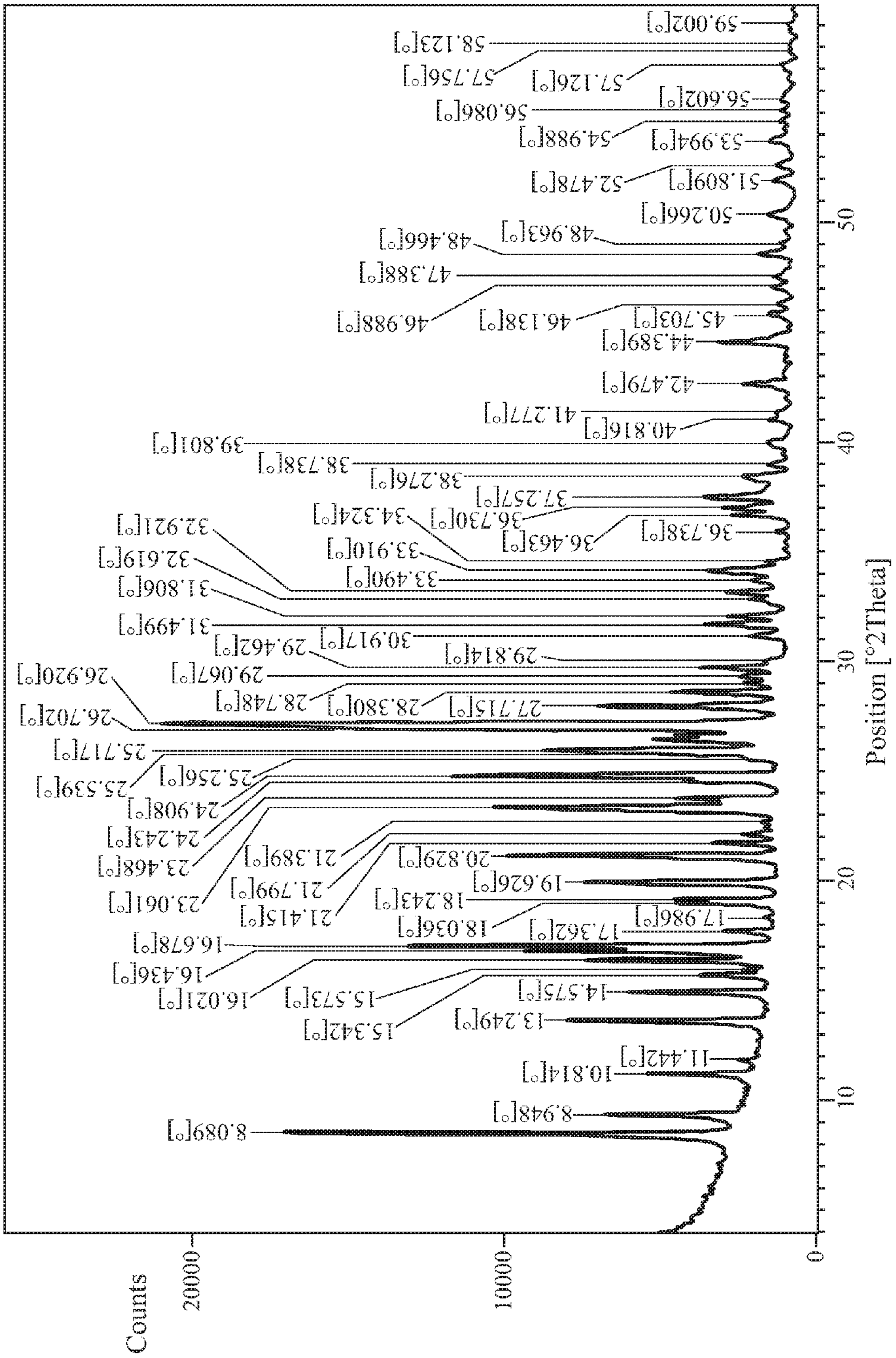
FIG. 2 is a powder X-ray diffractogram of an embodiment of crystalline modification I of diclosulam.

More particularly, the crystalline modification I of diclosulam of an embodiment of the invention is characterized by an X-ray powder diffractogram having at least three of the reflexes indicated above, in any combination thereof. Preferably, the crystalline modification I is one having at least four of the aforementioned reflexes, more preferably at least five, six or seven, or eight of said reflexes. An X-ray powder diffractogram of the crystalline modification I of diclosulam is shown in FIG. 2, which will be described in detail hereinafter.

According to a preferred embodiment the crystalline modification I exhibits at least 3, 4, or 5 or all of the reflexes, in any combination, as 2θ values in an X-ray powder diffractogram recorded using Cu-Kα radiation at 25° C. from the following:

2θ=8.09±0.2 (1)

2θ=13.25±0.2 (4)

2θ=16.68±0.2 (7)

2θ=20.83±0.2 (11)

2θ=23.06±0.2 (12)

2θ=24.51±0.2 (13)

2θ=25.72±0.2 (14)

2θ=26.70±0.2 (16)

2θ=26.92±0.2 (17)

The X-ray diffractogram was determined using a diffractometer from in reflection geometry in the range from 3°-60° with increments of 0.03° using Cu-Kα radiation at 25° C.

The crystalline modification I of diclosulam according to an embodiment may be further characterized by IR spectroscopy. The IR spectrum was measured with the resolution of 4 $cm^{-1}$ and with the number of scans of 16 for the purified sample. The IR spectrum of crystalline modification I of diclosulam can be identified by its characteristic functional group vibrations peaks at wavenumbers ($cm^{-1}$, ±0.2%) of about 3098.81, 2160.32, 2027.70, 1977.85, 1628.62, 1578.06 and 1515.70 $cm^{-1}$ as shown in FIG. 1.

All IR spectra were obtained using the following acquisition parameters:

| | |
|---|---|
| FT-IR spectrometer | Bruker Tensor37 |
| Diamond ATR unit | from Specac |
| Wavelength range | 550-4000 $cm^{-1}$ |
| Resolution | 4 $cm^{-1}$ |
| Number of scans | 16 |

Figure 3:
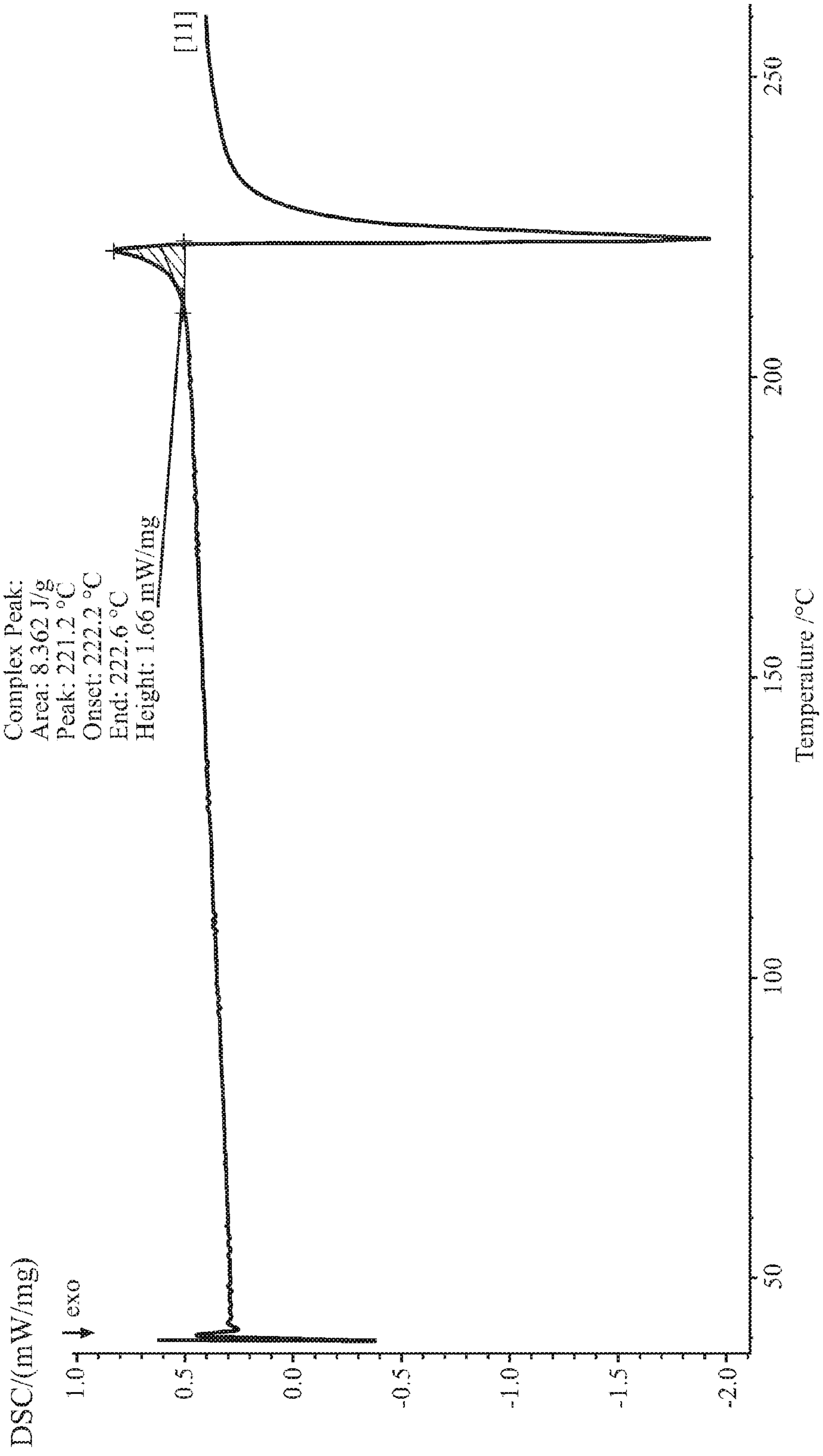
FIG. 3 is a Differential Scanning calorimetry (DSC) thermogram of an embodiment of crystalline modification I of diclosulam.

The crystalline modification I of diclosulam according to the invention may be further characterized by Differential Scanning calorimetry (DSC) (FIG. 3). An endothermic melting peak at about 221.2° C. is shown in FIG. 3.

Methods for preparing amorphous diclosulam are well known in the art. Amorphous diclosulam is manufactured and available on a commercial scale. A particularly suitable method for preparing amorphous diclosulam is described in U.S. Pat. No. 5,163,995.

According to an embodiment of the invention, the crystalline modification I of diclosulam can be obtained by the processes below:

Diclosulam in amorphous state is dissolved and then crystallized from solvents.

In one aspect, the present invention provides a process for preparing a crystalline modification I of diclosulam comprising steps of:

i) dissolving an amorphous diclosulam in a solvent;

ii) precipitating the dissolved compound into crystalline modification I of diclosulam; and iii) isolating the precipitated crystalline modification I.

Suitable solvents for preparation diclosulam crystalline modification I include: halogenated hydrocarbons (for example, chlorobenzene, bromobenzene, dichlorobenzene, chlorotoluene and trichlorobenzene), ethers (for example, ethyl propyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, methyl-tetrahydrofuran, polyethers of ethylene oxide and/or propylene oxide), nitrated hydrocarbons (for example, nitromethane, nitroethane, nitropropane, nitrobenzene, chloronitrobenzene and o-nitrotoluene), aliphatic, cycloaliphatic or aromatic hydrocarbons (for example, pentane, n-hexane, n-heptane, n-octane, nonane), cymene, petroleum fractions having a boiling range of from 70° C. to 190° C., cyclohexane, methylcyclohexane, petroleum ether, ligroin, octane, benzene, toluene and xylene), esters (for example, malonates, acetic acid n-butyl ester (n-butyl acetate), methyl acetate, ethyl acetate, isobutyl acetate, dimethyl carbonate, diethyl carbonate, dibutyl carbonate and ethylene carbonate), and aliphatic alcohols (for example, methanol, ethanol, n-propanol, isopropanol, n-butanol and tert-amyl alcohol), and mixtures thereof.

Preferred solvents include ethers, aromatic hydrocarbons, which can be optionally substituted with one or more substituents, which may be the same or different, selected from the group consisting of alkyl, optionally substituted by one or more halogens, which may be the same or different, nitro, halogen, ether, and the like (such as benzene, toluene, xylene, chlorobenzene), esters and aliphatic alcohols and mixtures thereof. Particularly preferred solvents or solvent mixtures include isopropanol, toluene, methyl-tetrahydrofuran, diethyl carbonate, chlorobenzene, n-butyl acetate, isobutyl acetate, n-butanol, methanol, ethanol, ethyl malonate, methyl t-butyl ether, and mixtures of toluene and butanol, toluene and n-butyl acetate, ethyl malonate and methyl t-butyl ether, as well as butyl acetate and methyl t-butyl ether. Solvent mixtures of more than 2 or 3 or 4 components are also envisaged by embodiments of the invention.

In an embodiment of the invention, it is preferred that the solvent comprises at least one alcohol, and more preferably comprises at least one straight or branched C1-C8 aliphatic alcohol, more preferably at least one straight or branched C1-C4 aliphatic alcohol, even more preferably at least one of methanol and ethanol.

According to another preferred embodiment, the solvent essentially consists of an alcohol as mentioned above or mixtures thereof.

Hence, according to a preferred embodiment in step (i), amorphous diclosulam is dissolved in a solvent comprising an alcohol. In a preferred embodiment, the solvent essentially consists of methanol and/or ethanol or other primary alcohols preferably with boiling range below 100° C.

According to a preferred embodiment in step (i), an amorphous diclosulam is dissolved in a solvent or a solvent mixture as a concentrated solution by heating from room temperature or ambient temperature to reflux temperature or below the reflux temperature of the solvent or the solvent mixture. Preferably, the concentrated solutions can be prepared at the reflux temperature of the solvents. The concentration of the solution depends on the solubility of diclosulam in the corresponding solvent or solvent mixture.

The concentrated homogeneous solution thus prepared as in step (i) is then cooled to room or ambient temperature or to a temperature of around 0° C. to 20° C. to crystallize the desired crystalline form from the solvent. The crystalline modification I of diclosulam can also be crystallized out by concentrating the homogeneous solution through removing the solvent or solvent mixture to certain volume with or without applying vacuum and cooling to below the reflux temperature of the solvent or the solvent mixture.

In another embodiment, crystalline modification I of diclosulam can also be effected by adding seed crystals of the desired crystalline form during crystallization into a solution prepared in step (i), which can promote and/or accelerate the crystallization.

The seed crystal amount added to the concentrated solution is typically in the range of 0.001 to 10% by weight, preferably 0.001 to 2.5%, more preferably 0.005 to 0.5% by weight based on the weight of diclosulam used for the preparation of concentrated solution in step (i). Preferably, the seed crystals are added to the concentrated solution at the temperature below the boiling point of the corresponding solvent or the solvent mixture.

Hence, the precipitation of the crystalline modification I of diclosulam can be effectively achieved from the concentrated solution by a person of ordinary skill in the art.

The precipitated crystalline modification I of diclosulam obtained from step (ii) is isolated by the usual solid component separating techniques from solutions, such as filtration, centrifugation or decantation. Then, the isolated solid is washed with solvent one or more times. Preferably, the solvent employed in the washing stage consists of one or more components of the solvent or solvent mixture employed for preparation of concentrated solution in step (i), as described hereinbefore. The washing is usually carried out using the corresponding solvent or solvent mixture between room temperature and 0° C. depending on the solubility of the crystal in order to minimize or avoid the loss of crystalline material in the corresponding washing solvent in the corresponding washing solvent as much as possible.

The invention, in an embodiment, also relates to a composition comprising the crystalline modification I of diclosulam. The amount of the crystalline modification I of diclosulam is less than 75% by weight of the composition, preferably less than 50% by weight of the composition, more preferably less than 30% by weight of the composition, still more preferably about 25% by weight of the composition.

The use of amorphous diclosulam as a herbicide is known in the art and is used on a commercial scale. The crystalline modification I of diclosulam is also active in controlling unwanted plant growth, such as weeds. Techniques of formulating and applying amorphous diclosulam are known in the art, for example as disclosed in the documents described hereinbefore. Diclosulam in the crystalline modification I of the present invention may be formulated and applied in manner analogous to those described for amorphous diclosulam.

Accordingly, in a further aspect, an embodiment of the invention provides a herbicidal composition comprising diclosulam in the crystalline modification I as defined hereinbefore.

Accordingly, an embodiment of the invention furthermore provides processes for preparing compositions for controlling unwanted plant growth using the crystalline modification I of diclosulam.

Accordingly, the invention also provides a method for controlling unwanted plant growth, comprising applying to the plant, plant part, or surroundings of the plant, a herbicidally effective amount of crystalline modification I of diclosulam.

The crystalline modification I of diclosulam can be incorporated into the customary formulations, such as suspension concentrates (SC), oil-based suspension concentrates (OD), water-soluble granules (SG), dispersible concentrates (DC), emulsifiable concentrates (EC), emulsion seed dressings, suspension seed dressings, granules (GR), microgranules (MG), suspoemulsions (SE) and water-dispersible granules (WG) using suitable auxiliaries, carriers and solvents, in a manner analogous to that known for amorphous diclosulam.

In this context, the crystalline modification I of diclosulam may be present in a concentration of from about 0.1 to about 50% by weight of the total mixture, i.e., in amounts sufficient to achieve the required dosage. The formulations are prepared, for example, by extending the crystalline modification I of diclosulam with water, solvents and carriers, using, if appropriate, emulsifiers and/or dispersants, and/or other auxiliaries.

These formulations are prepared by mixing the crystalline modification I of diclosulam with at least one acceptable auxiliaries, for example, surfactants, liquid diluents, solid diluents, wetting agents, dispersants, thickening agent, antifoaming agent and other formulation ingredients.

Liquid diluents include, but are not limited to, water, N,N-dimethylamide, dimethyl sulfoxide, N-alkylpyrrolidone, ethylene glycol, polypropylene glycol, propylene carbonate, dibasic esters, paraffines, alkylbenzenes, alkyl naphthalenes, glycerine, triacetin, oils of olive, castor, linseed, sesame, corn, peanut, cotton-seed, soybean, rape-seed and coconut, ketones such as cyclohexanone, 2-heptanone, isophorone and 4-hydroxy-4-methyl-2-pentanone, acetates such as hexyl acetate, heptyl acetate and octyl acetate, and alcohols such methanol, cyclohexanol, decanol, benzyl and tetrahydrofurfuryl alcohol, and mixtures thereof.

Solid diluents can be water-soluble or water-insoluble. Water-soluble solid diluents include, but are not limited to, salts such as alkali metal phosphates (e.g., sodium dihydrogen phosphate), alkaline earth phosphates, sulfates of sodium, potassium, magnesium and zinc, sodium and potassium chloride, sodium acetate, sodium carbonate and sodium benzoate, and sugars and sugar derivatives such as sorbitol, lactose, sucrose and mannitol. Examples of water-insoluble solid diluents include, but are not limited to clays, synthetic and diatomaceous silicas, calcium and magnesium silicates, titanium dioxide, aluminum, calcium and zinc oxide, and mixtures thereof.

Wetting agents include, but are not limited to, alkyl sulfosuccinates, laureates, alkyl sulfates, phosphate esters, acetylenic diols, ethoxyfluorinated alcohols, ethoxylated silicones, alkyl phenol ethyoxylates, benzene sulfonates, alkyl-substituted benzene sulfonates, alkyl α-olefin sulfonates, naphthalene sulfonates, alkyl-substituted napthalene sulfonates, condensates of naphthalene sulfonates and alkyl-substituted naphthalene sulfonates with formaldehyde, and alcohol ethoxylates, and mixtures thereof. Alkyl naphthalene sulphonates, sodium salts are particularly useful for the composition of the invention.

Dispersants include, but are not limited to, sodium, calcium and ammonium salts of ligninsulfonates (optionally polyethoxylated); sodium and ammonium salts of maleic anhydride copolymers; sodium salts of condensed phenolsulfonic acid; and naphthalene sulfonate-formaldehyde condensates. Ligninsulfonates such as sodium ligninsulfonates are particularly useful for the composition of the invention. Naphthalene sulfonate-formaldehyde condensates such as Naphthalenesulfonic acid, polymers with formaldehyde, and sodium salts are particularly useful for the composition of the invention.

Thickening agents include, but are not limited to, guar gum, pectin, casein, carrageenan, xanthan gum, alginates, methylcellulose, hydroxyethylcellulose, hydroxypropylcellulose, and carboxymethylcellulose, and mixtures thereof. Synthetic thickening agents include derivatives of the former categories, and also polyvinyl alcohols, polyacrylamides, polyvinylpyrrolidones, various polyethers, their copolymers as well as polyacrylic acids and their salts, and mixtures thereof. Alkylpolyvinylpyrrolidones are particularly useful for the composition of the invention.

Other formulation ingredients can also be used in the present invention such as dyes, drying agents, and the like. These ingredients are known to one skilled in the art.

The crystalline modification I of diclosulam according to an embodiment of the invention can be present in formulations and in its use forms, prepared from these formulations, and as a mixture with one or more of other active compounds (such as insecticides, attractants, sterilizing agents, bactericides, acaricides, nematicides, fungicides, growth-regulating substances, herbicides, safeners, fertilizers and semiochemicals) or with agents for improving plant properties.

When used as herbicide, the crystalline modification I of diclosulam according to an embodiment of the invention can furthermore be present in formulations and its use forms, prepared from these formulations, and as a mixture with inhibitors which reduce degradation of the active compounds after their use in the environment of the plant, on the surface of plant parts or in plant tissues.

All plants, plant parts, and their surroundings can be treated in accordance with the invention. In the present context, plants are to be understood as meaning all plants and plant populations such as desired and undesired wild plants or crop plants (including naturally occurring crop plants). Crop plants can be plants which can be obtained by conventional breeding and optimization methods, by biotechnological and genetic engineering methods, or by combinations of these methods, including the transgenic plants and the plant cultivars which can or cannot be protected by plant breeders' rights. Plant parts are to be understood as meaning all parts and organs of plants above and below the ground, such as shoot, leaves, needles, stalks, stems, flowers, fruit bodies, fruits, seeds, roots, tubers and rhizomes. Harvested materials, and vegetative and generative propagation materials, for example, cutting, tubers, meristem tissue, rhizomes, offsets, seeds, single and multiple plant cells and any other plant tissues, are also included.

As used herein, the term "about," when used in connection with a numerical amount or range, means somewhat more or somewhat less than the stated numerical amount or range, to a deviation of ±10% of the stated numerical amount or endpoint of the range.

"Surrounding," as used herein, refers to the place on which the plants are growing, the place on which the plant propagation materials of the plants are sown or the place on which the plant propagation materials of the plants will be sown, or the environment near the plants.

The term "herbicidally effective amount" as used herein, refers to the quantity of such a compound or combination of such compounds that is capable of producing a controlling effect on the growth of plants. The controlling effects include all deviation from the natural development of the target plants, for example killing, retardation of one or more aspects of the development and growth of the plant, leaf burn, albinism, dwarfing and the like.

Treatment according to an embodiment of the invention of the plants, plant parts and/or their surroundings, with the compositions or formulations of the inventions is carried out directly or by allowing the compositions or formulations to act on their surroundings, habitat or storage space by the customary treatment methods. Examples of these customary treatment methods include dipping, spraying, vaporizing, fogging, broadcasting, painting on in the case of propagation material, and applying one or more coats particularly in the case of seed.

The benefits of the invention are seen most when the herbicidal composition is applied to kill weeds in growing crops of useful plants: such as peanuts, soya beans, maize (corn) including field corns, pop corns and sweet corns, cotton, wheat, rice, oats, potatoes, sugar beets, plantation crops (such as bananas, fruit trees, rubber trees, tree nurseries), vines, citrus, olive, amenity, asparagus, bushberries (such as blueberries), caneberries, cranberries, flax, grain sorghum, okra, peppermint, rhubarb, spearmint, turf grass and sugarcane. In this invention, treatment of peanuts and soya beans are particularly beneficial.

All percentages are given in weight % unless otherwise indicated.

Embodiments of the invention will now be described by the following examples which are provided for illustrative purposes only, and not intended to limit the scope of the disclosure.

EXAMPLES

Example 1: Preparation of Amorphous Diclosulam in Accordance with the Disclosure of U.S. Pat. No. 5,163,995 with Modification in Example 13

Anhydrous sodium iodide (11.7 g, 0.078 mol) was placed in 50 ml of dry acetonitrile and 8.5 g (0.078 mol) of trimethylsilyl chloride added with stirring. To this mixture was added 6.3 g (0.039 mol) of 2,6-dichloroaniline and 7.9 g (0.078 mol) of triethylamine. This resultant mixture was continuously and slowly stirred at ambient temperature for 30 min and then the volatiles were carefully removed by evaporation under reduced pressure and the residue diluted with ether and filtered. The contents of this solution appeared to be N-trimethylsilyl-2,6-dichloroaniline of about 97 percent purity by GLC analysis. The ether precipitation of insolubles was repeated and the ether was removed by evaporation under reduced pressure. The residue was mixed with 50 ml of dry acetonitrile, 3.9 g (0.013 mol) of 7-fluoro-2-chlorosulfonyl-5-ethoxy-1,2,4-triazolo[1,5-c]pyrimidine, and 0.2 ml (0.003 mol) of dimethylsulfoxide and the mixture was slowly and steadily stirred overnight. The resulting mixture was concentrated under reduced pressure and the solid residue was mixed with hexane and water and filtered. The resultant residue was then dissolved in 400 ml of methylene chloride and the solution was extracted with water and aqueous part was removed. The remaining organic component is dried over sodium sulfate and filtered. It was then concentrated under reduced pressure and the residue was mixed with hexane, collected by filtration, and dried to obtain 3.3 g (60 percent of theory) of the title compound.

Figure 4:
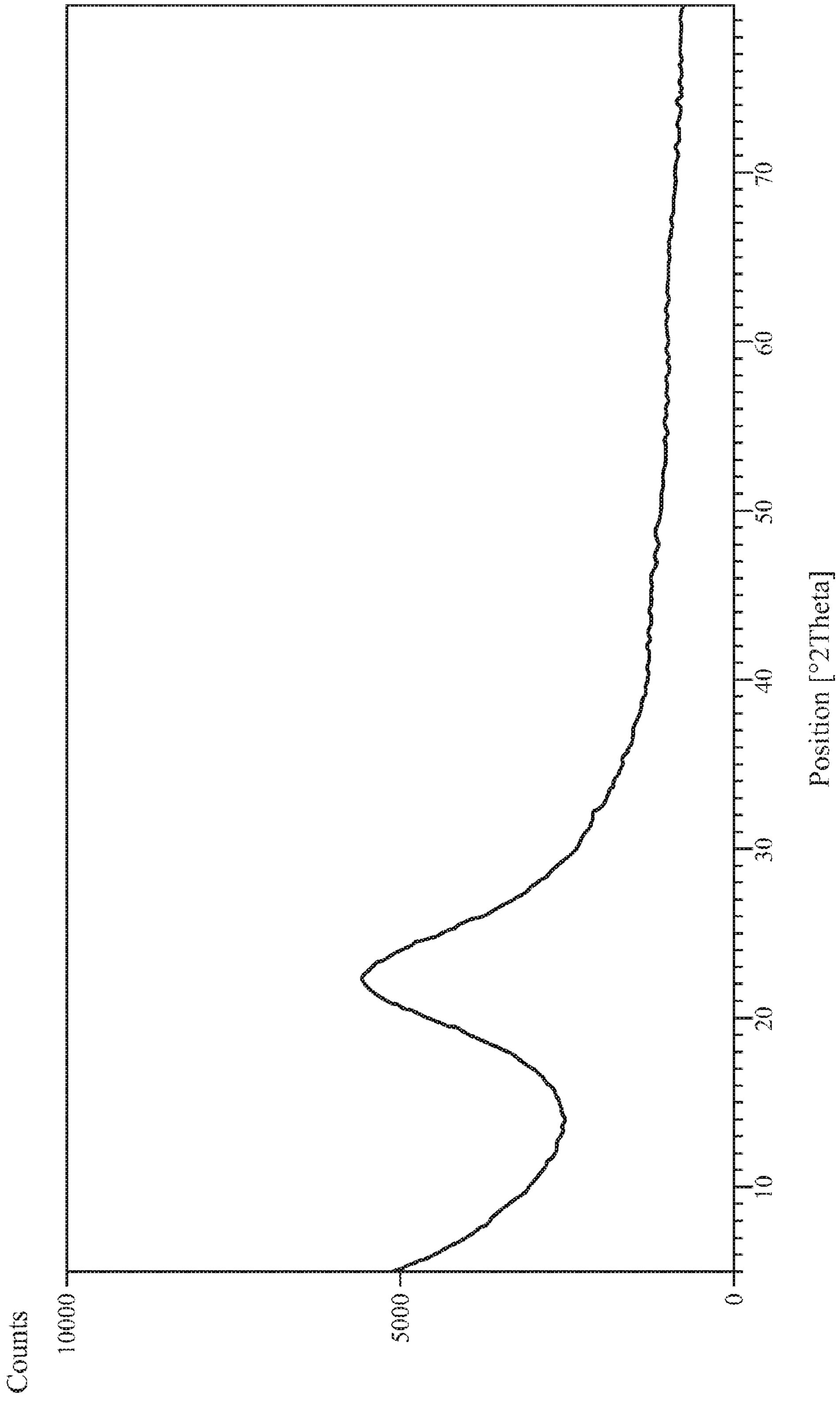
FIG. 4 is a powder X-ray diffractogram of amorphous diclosulam.

As shown in FIG. 4, the X-ray powder diffraction pattern of the resulting diclosulam product has no significant individual signals or peaks, which indicates the diclosulam product prepared in accordance with the disclosure of U.S. Pat. No. 5,163,995 is amorphous.

Preparation of Crystalline Modification I of Diclosulam

Example 2—Crystallization from Methanol

Diclosulam sample as prepared in above Example 1 (10 g) was taken in a three-neck round bottom flask along with methanol (60 mL) and the resulting slurry was heated to 50° C. to get a homogeneous solution. The insoluble particles, if any, were filtered and the solution was slowly cooled to room temperature. Upon cooling, fine crystals were formed and the heterogeneous mixture was stirred at room temperature for 2 h. Then, the slurry was filtered and washed with method (3 mL). The filtered crystals were dried under vacuum in order to remove the method traces from the crystalline product. The crystalline product thus obtained was having a purity of >98% and the recovered product as crystal was found to be not less than 80% (w/w) quantitative yield.

The obtained crystal was analyzed by IR, X-ray powder diffraction and DSC, and found out to be crystalline modification I of diclosulam as shown in FIGS. 1, 2 and 3, respectively.

The Differential scanning calorimetry (DSC) (FIG. 3) shows endothermic melting peak at about 221.2° C. in FIG. 3.

The IR spectrum of diclosulam shows the functional group vibrations peaks at wavenumbers ($cm^{-1}$, ±0.2%) of about 3098.81, 2160.32, 2027.70, 1977.85, 1628.62, 1578.06 and 1515.70 $cm^{-1}$ in FIG. 1.

The powder X-ray diffractogram of crystals shows the reflexes in FIG. 2 and the values are summarized in Table 1. The X-ray powder diffractogram were taken using a diffractometer in reflection geometry in the range from 3°-60° with increments of 0.03° using Cu-Kα radiation at 25° C.

TABLE 1

Powder X-ray diffractogram reflexes of crystalline modification I of Diclosulam crystalline modification I

| 2 θ (°) | d (Å) |
|---|---|
| 8.09 ± 0.2 | 10.93 ± 0.05 |
| 8.95 ± 0.2 | 9.88 ± 0.05 |
| 10.81 ± 0.2 | 8.18 ± 0.05 |
| 13.25 ± 0.2 | 6.68 ± 0.05 |
| 16.02 ± 0.2 | 5.53 ± 0.05 |
| 16.44 ± 0.2 | 5.39 ± 0.05 |
| 16.68 ± 0.2 | 5.32 ± 0.05 |
| 18.64 ± 0.2 | 4.76 ± 0.05 |
| 18.82 ± 0.2 | 4.71 ± 0.05 |
| 19.63 ± 0.2 | 4.52 ± 0.05 |
| 20.83 ± 0.2 | 4.26 ± 0.05 |
| 23.06 ± 0.2 | 3.86 ± 0.05 |
| 24.51 ± 0.2 | 3.63 ± 0.05 |
| 25.72 ± 0.2 | 3.46 ± 0.05 |
| 26.15 ± 0.2 | 3.41 ± 0.05 |
| 26.70 ± 0.2 | 3.34 ± 0.05 |
| 26.92 ± 0.2 | 3.31 ± 0.05 |
| 27.72 ± 0.2 | 3.22 ± 0.05 |

Example 3—Crystallization from Ethanol

Diclosulam (5 g) sample prepared in Example 1 was taken in a three-neck round bottom flask along with ethanol (35 mL) and the resulting slurry was heated to 60° C. or to reflux temperature to get a homogeneous solution. The resultant hot solution was filtered to remove the insoluble (if any) and the solution was slowly cooled to ambient temperature. Product was precipitated out as fine crystal during cooling and the mixture was stirred at room temperature for 2 to 3 hours. Then, the slurry was filtered, washed with ethanol (3 mL) and dried under vacuum at room temperature in order to remove the ethanol traces from the crystal. The crystal thus obtained was having a purity of >98% and the recovered yield was found to be not less than 80%.

The crystals were characterized as being diclosulam crystalline modification I using infra-red spectrometry, X-ray diffraction and DSC, as described in Example 2.

Example 4: Preparation of Oil Based Suspension Concentrate (OD) Formulation

All the components listed in Table 2 below were mixed uniformly and ground with a Dyno-Mill (manufactured by Willy A. Bachofen AG) to obtain an oil based suspension concentrate (OD).

TABLE 2

| Ingredients | Weights % | | Function |
|---|---|---|---|
| Diclosulam, crystalline modification I, 98% (prepared in Example 2) | 40.8 | 0 | Active compound |
| Amorphous diclosulam (prepared in Example 1) | 0 | 40.8 | Active compound |
| Modified polyether-polysiloxane | 0.5 | 0.5 | Antifoaming agent |
| Ethoxylated castor oil | 15 | 15 | Emulsifier |
| Sodium alkylnaphthalenesulfonate, formaldehyde | 5 | 5 | Dispersing agent |
| Silica | 2 | 2 | Thickening agent |
| Corn oil | Balance to 100% | Balance to 100% | Carrier |

Example 5: Preparation of Soluble Granules (SG)

All the components listed in Table 3 below were mixed, blended and milled in a high-speed rotary mill. Sufficient water was added to obtain an extrudable paste. The resultant mass is passed through and extruded through a die or screen to form an extrudate. The wet extrudate mass was dried at 70° C. in a vacuum oven and then sifted through 0.71 mm-2 mm screens to obtain the product granules.

TABLE 3

| Ingredients | Weights % | | Function |
|---|---|---|---|
| Diclosulam, crystalline modification I, 98% (prepared in Example 2) | 25.51 | 0 | Active compound |
| Amorphous diclosulam (prepared in Example 1) | 0 | 25.51 | Active compound |
| Lignosulfonic acid, sodium salt, (REAX ® 88B) | 5 | 5 | Antifoaming agent |
| Sodium lauryl sulfate | 0.5 | 0.5 | Wetting agent |
| Sodium hydrogen carbonate | 2 | 2 | Filler |
| Potassium sulfate | Balance to 100% | Balance to 100% | carrier |

Example 6: Preparation of Water Dispersible Granules (WG)

All the components listed in Table 4 below were mixed, blended and milled in a high-speed rotary mill. Sufficient water were added to obtain an extrudable paste. The paste was extruded through a die or screen to form an extrudate. The wet extrudate was dried at 70° C. in a vacuum oven and then sifted through 0.71 mm-2 mm screens to obtain the product granules.

TABLE 4

| Ingredients | Weights % | | Function |
|---|---|---|---|
| Diclosulam, crystalline modification I, 98% (prepared in Example 2) | 25.51 | 0 | Active compound |
| Amorphous diclosulam (prepared in Example 1) | 0 | 25.51 | Active compound |
| Alkyl naphthalene sulphonate, sodium salt (Akzo Nobel) | 2 | 2 | Wetting agent |
| Lignosulfonic acid, sodium salt, REAX ® 88B) | 15 | 15 | Dispersing agent |
| Naphthalenesulfonic acid, polymer with formaldehyde, sodium salt (TAMOL ® NN8906) | 6 | 6 | Dispersing agent |
| Non-ionic aqueous emulsion of Polydimethylsiloxanes | 1 | 1 | Antifoaming agent |
| Mannitol | Balance to 100% | Balance to 100% | Carrier |

Example 7: Determining Water Solubility

A stock pH 7 buffer solution was prepared by adding aqueous sodium hydroxide solution (0.1 M, 145 mL) to aqueous potassium dihydrogen phosphate solution (0.1 M, 250 mL), and then adding sufficient distilled water to adjust the final volume to 500 mL. At least 1 time and up to about 5 times the amount of diclosulam needed for saturation was added to a mixing vessel containing stock buffer solution at the test temperature (e.g., 20° C.). The mixture was magnetically stirred in the dark while being maintained at the test temperature and the samples were intermittently and periodically removed for analysis. The samples were centrifuged using a high speed, temperature-controlled centrifuge at the test temperature for about 20 minutes at ≥12000 G to remove suspended particles. An aliquot of each supernatant was taken for analysis.

The concentration of diclosulam in the supernatant was determined by a high pressure liquid chromatography (HPLC) with a reversed phase chromatography column and UV detection. The method should include development of best-fit calibration curves based on at least three standards using linear regression analysis Samples were successively withdrawn from the mixing vessel and analyzed until three successive samples show little or no variation in concentration. The test is preferably replicated to ensure accuracy.

TABLE 5

| Sample | Formulation | Original concentration, % | Concentration measured by HPLC after treatment, % | Solubility |
|---|---|---|---|---|
| Diclosulam, crystalline modification I, 98% (prepared in Example 2) | OD | 40 | 35 | 87.5% |
| Amorphous diclosulam (prepared in Example 1) | OD | 40 | 14 | 35% |
| Diclosulam, crystalline modification I, 98% (prepared in Example 2) | SG | 25 | 24.9 | 99.6% |
| Amorphous diclosulam (prepared in Example 1) | SG | 25 | 15 | 60% |
| Diclosulam, crystalline modification I, 98% (prepared in Example 2) | WG | 25 | 23 | 92% |
| Amorphous diclosulam (prepared in Example 1) | WG | 25 | 12 | 48% |

Example 8: Cleanout Test

The test was conducted by dispersing in water a sample to produce a concentration that is normally used when applying the herbicide: 25% diclosulam. The sample was added to tap water (300 mL) in a 400 mL beaker and magnetically stirred for 2 minutes. The mixture was then stirred for 2 minutes, whereupon the resulting dispersion was dispensed in three 100 mL aliquots to 4-oz (118 mL) polyethylene bottles. The bottles were capped, inverted 2-3 times and allowed to stand overnight.

After standing overnight, each individual bottle was inverted twice and the liquid contents were then poured out. Tap water (10 mL) was added and the bottle was inverted until all sediment was re-suspended, whereupon the contents were poured out. Tap water (100 mL) was added and the bottle was inverted twice and then allowed to stand undisturbed for 10 minutes. The bottle was inverted twice more and the contents were poured out. Acetonitrile (10 mL) was added to the bottle to extract any remaining material. The acetonitrile solution was analyzed by reversed-phase liquid chromatography with UV detection. The cleanout rating (the concentration of diclosulam herbicide in the acetonitrile solution) is reported in % in Table 6 below. Lower cleanout ratings indicate more effective cleanout compared to higher ratings.

TABLE 6

| Sample | Formulation | Cleanout rating, % |
|---|---|---|
| Diclosulam, crystalline modification I, 98% (prepared in Example 2) | OD | 5 |

TABLE 6-continued

| Sample | Formulation | Cleanout rating, % |
|---|---|---|
| Amorphous diclosulam, prepared in Example 1 | OD | 26 |
| Diclosulam, crystalline modification I, 98% (prepared in Example 2) | SG | 0.1 |
| Amorphous diclosulam, prepared in Example 1 | SG | 10 |
| Diclosulam, crystalline modification I, 98% (prepared in Example 2) | WG | 2 |
| Amorphous diclosulam (prepared in Example 1) | WG | 13 |

Although methanol and ethanol are exemplified above as solvents to produce crystalline modification I of diclosulam, other solvents disclosed herein are also suitable for producing this crystalline modification using the procedures described herein, or such modifications thereof as would be apparent to one of ordinary skill in this art in possession of the above disclosure.

The invention claimed is:

1. A crystalline modification I of diclosulam (2',6'-dichloro-5-ethoxy-7-fluoro[1,2,4]triazolo[1,5-c]pyrimidine-2-sulfonanilide) exhibiting each of the following reflexes as 2θ values in X-ray powder diffractogram recorded using Cu-Kα radiation at 25° C.:

$$2\theta=8.09\pm0.2 \quad (1)$$

$$2\theta=8.95\pm0.2 \quad (2)$$

$$2\theta=10.81\pm0.2 \quad (3)$$

$$2\theta=13.25\pm0.2 \quad (4)$$

$$2\theta=16.02\pm0.2 \quad (5)$$

$$2\theta=16.44\pm0.2 \quad (6)$$

$$2\theta=16.68\pm0.2 \quad (7)$$

$$2\theta=18.64\pm0.2 \quad (8)$$

$$2\theta=18.82\pm0.2 \quad (9)$$

$$2\theta=19.63\pm0.2 \quad (10)$$

$$2\theta=20.83\pm0.2 \quad (11)$$

$$2\theta=23.06\pm0.2 \quad (12)$$

$$2\theta=24.51\pm0.2 \quad (13)$$

$$2\theta=25.72\pm0.2 \quad (14)$$

$$2\theta=26.15\pm0.2 \quad (15)$$

$$2\theta=26.70\pm0.2 \quad (16)$$

$$2\theta=26.92\pm0.2 \quad (17)$$

$$2\theta=27.72\pm0.2 \quad (18).$$

2. The crystalline modification I of diclosulam according to claim 1, exhibiting an IR spectrum with characteristic functional group vibrations peaks at wavenumbers ($cm^{-1}$, ±0.2%) of about 3098.81, 2160.32, 2027.70, 1977.85, 1628.62, 1578.06 and 1515.70 $cm^{-1}$.

3. The crystalline modification I of diclosulam according to claim 1 exhibiting a Differential Scanning calorimeter (DSC) thermogram having an endothermic melting peak at about 221.2° C.

4. A process of preparing crystalline modification I of diclosulam according to claim 1, comprising:

i) dissolving an amorphous diclosulam in a solvent, wherein the solvent is methanol, ethanol, or a mixture thereof;

ii) precipitating the dissolved compound into the crystalline modification I of diclosulam; and iii) isolating the precipitated crystalline modification I.

5. The process according to claim 4, wherein step ii) is effected by concentration of the solvent or by cooling to ambient temperature of around 0 to 20° C., or by adding seed crystals of the crystalline modification I, or a combination thereof.

6. A crystalline modification I of diclosulam obtained according to claim 4, wherein crystalline modification I of diclosulam has a purity at least 98% by weight.

7. A composition comprising an herbicidally effective amount of the crystalline modification I of diclosulam according to claim 1, and at least one auxiliary.

8. The composition according to claim 7, wherein the auxiliary is selected from one or more of a surfactant, a diluent, a wetting agent, a dispersant, a thickening agent and an antifoaming agent.

9. The composition according to claim 7, in the form of a suspension concentrate (SC), an oil-based suspension concentrate (OD), a water-soluble granule (SG), a dispersible concentrate (DC), an emulsifiable concentrate (EC), an emulsion seed dressing, a suspension seed dressing, a granule (GR), a microgranule (MG), a suspoemulsion (SE) or a water-dispersible granule (WG).

10. The composition according to claim 9 in the form of an oil-based suspension concentrate (OD), a water-dispersible granule (WG) or a water-soluble granule (SG).

11. A method for controlling unwanted plant growth, comprising applying to the plant, plant part, or surroundings of the plant, a herbicidally effective amount of crystalline modification I of diclosulam according to claim 1.

* * * * *